US007783133B2

(12) United States Patent
Dunki-Jacobs et al.

(10) Patent No.: US 7,783,133 B2
(45) Date of Patent: Aug. 24, 2010

(54) ROTATION COMPENSATION AND IMAGE STABILIZATION SYSTEM

(75) Inventors: Robert J. Dunki-Jacobs, Mason, OH (US); Frank B. Metting, III, Bothell, WA (US); Selso Luanava, Woodinville, WA (US)

(73) Assignees: Microvision, Inc., Redmond, WA (US); Ethicon Endo-Surgery, Inc., Cincinnati, OH (US)

( * ) Notice: Subject to any disclaimer, the term of this patent is extended or adjusted under 35 U.S.C. 154(b) by 908 days.

(21) Appl. No.: 11/648,857

(22) Filed: Dec. 28, 2006

(65) Prior Publication Data
US 2008/0159653 A1  Jul. 3, 2008

(51) Int. Cl.
*G06K 9/32* (2006.01)

(52) U.S. Cl. ............... 382/296; 382/100; 382/128; 382/293; 600/101; 600/103; 600/118; 600/173

(58) Field of Classification Search ............... 382/100, 382/128, 293, 296; 600/101, 103, 109, 110, 600/112, 117, 118, 138, 139, 160, 173
See application file for complete search history.

(56) References Cited

U.S. PATENT DOCUMENTS

| | | | | |
|---|---|---|---|---|
| 6,160,578 A | * | 12/2000 | Carroll et al. | 348/222.1 |
| 6,471,637 B1 | * | 10/2002 | Green et al. | 600/109 |
| 6,574,355 B2 | * | 6/2003 | Green | 382/128 |
| 7,387,605 B2 | * | 6/2008 | Frith | 600/112 |
| 7,517,314 B2 | * | 4/2009 | Hoeg et al. | 600/117 |
| 2002/0161280 A1 | * | 10/2002 | Chatenever et al. | 600/112 |
| 2003/0142934 A1 | * | 7/2003 | Pan et al. | 385/116 |
| 2004/0076341 A1 | * | 4/2004 | Dolan | 382/289 |
| 2007/0197871 A1 | * | 8/2007 | Geitz et al. | 600/117 |

* cited by examiner

*Primary Examiner*—Matthew C Bella
*Assistant Examiner*—Eric Rush
(74) *Attorney, Agent, or Firm*—Kevin D. Wills

(57) ABSTRACT

An image processing system is arranged to provide rotation compensation and image stabilization in a video scope system such as in endoscopy and laparoscopy systems. The image processing functions may operate at real-time frame rates so that the resulting processed image is observable with no time lag. A rotation sensor is included in the system to sense the position of scope. The sensed scope rotation may be used to cause rotation of the collected image and/or an image displayed on a video monitor. The sensed rotation may be used to identify or calculate a coordinate transformation matrix that is used for processing the image data. The system may include a horizon lock mechanism that can be user-actuated to engage rotation compensation. When the horizon lock mechanism is not engaged, the output image is locked to the scope tip and rotates with rotation of the scope.

6 Claims, 11 Drawing Sheets

ROTATION COMPENSATION AND IMAGE STABILIZATION SYSTEM

FIELD OF THE INVENTION

The present disclosure generally relates to image scanning systems. More particularly, the present disclosure relates to a system and method for compensating and stabilizing an image in an environment where the orientation of an image is rotating and moving relative to a horizon. The described imaging system and method are useful in endoscopy and laparoscopy applications.

BACKGROUND

Video endoscopes and laparoscopes have been in general use since the 1980s. Laparoscopes are rigid devices that may be used in minimally invasive diagnostic and surgical procedures. In contrast, endoscopes are flexible devices that may be used in invasive diagnostic and surgical procedures. While the implementation of an endoscope and a laparoscope are different from one another, endoscopy and laparoscopy systems are both arranged to capture optical signals and generate a video image.

A typical laparoscopy system includes a hand-tool and a console with a video display. The body of the hand-tool includes a long rigid tube with a digital camera that is mounted proximal to an end of the tube. A series of rod lenses form an array that extends from an end of the tube to the digital camera so that a video image can be collected when the tube is extended into a body cavity of a patient. The digital camera communicates the collected video image to the console through a series of wires that also extend through the tube such that the video image can be viewed on the video display. Also typically, a light source is mounted on the console that is based on a xenon lamp. Light from the light source is coupled to the laparoscope tube through a fiber optic coupling. Optical fibers extend though the length of the laparoscope tube to a distal end where a concentric ring, or partial arc is formed to provide an appropriate illumination for the video image. The illumination power can be adjusted at the console to provide an image with an appropriate brightness level for the video display.

A typical endoscopy system also includes a hand-tool and a console with a video display. The body of the hand-tool includes a hand piece that is connected to a long flexible tube with a digital camera that is mounted at a distal end of the tube. The digital camera is arranged to capture light, convert the captured light into an electronic signal, and send the electronic signal through the flexible tube to the hand piece. The hand piece is arranged to send the electronic image to the console, where the image can be viewed on the digital display. The light source for the endoscope is also mounted on the console and based on a xenon lamp, with light being coupled to the endoscope tube through a fiber optic coupling. Optical fibers extend though the length of the laparoscope tube to a distal end, where the optical fibers terminate as apertures that are located about the camera lens.

Endoscopes and laparoscopes can be end-looking or side-looking. End-looking devices have a field-of-view that is positioned directly in front of the end of the device. Side-looking devices can have their field-of-view located at 70°, or some other angle that is off-axis from the end of the tube. The field-of-view varies according to the particular application. For example, a colonoscope often has a 140° diagonal field-of-view, while a laparoscope may have a field-of-view that is closer to 70° diagonal.

The basis of the digital camera devices in both endoscopy and laparoscopy systems is typically a solid-state focal plane sensor array such as a charge-coupled device (CCD) or a complementary metal-oxide semiconductor (CMOS) device. The pixelated, focal plane sensor array consists of an array of light-sensitive elements that develop an electrical charge when exposed to light from a conjugate point in the field-of-view. An electrical charge is accumulated by a light-sensitive element over a selected sampling interval that corresponds to a shutter or exposure time. The accumulated electrical charge for the light-sensitive element is indicative of the brightness level for the corresponding conjugate point from the field of view for the selected sampling interval. The accumulated electrical charge associated with the light-sensitive element can be amplified, transmitted, processed, displayed, and recorded.

Typically, a light-sensitive element contributes to a unit or pixel of the total image. The resolution or clarity of the image depends upon the total number of pixels or light receptors that are in the sensor array. Standard cameras used for laparoscopy or endoscopy contain between 250,000 and 380,000 pixels. The clarity of the image that is eventually displayed or recorded depends upon both the sensor array resolution and the resolution capability of the monitor, as well as another resolution that is associated with a recording medium. Standard consumer-grade video monitors have 350 lines of horizontal resolution, while monitors that are preferred for surgical applications have about 700 lines of resolution.

Endoscopes often include irrigation channels and working channels for instruments, in addition to a steering apparatus that can be used to aim and push or pull the tip of the endoscope toward a targeted area in the patient under the direction of a clinician. Instruments such as forceps, scissors, needle drivers, and other devices have been developed to pass through the working channel of the endoscope for use by a clinician for a variety of uses such as taking tissue samples, delivering medicine, etc. In contrast, laparoscopes typically do not typically include working channels and necessary instruments are typically introduced to the procedure through a separate small incision in the patient. Laparoscopes include facility to pass certain very small instruments such as trocars or rings that line the incisions to prevent undue binding or damage as well as maintain a seal.

During a diagnostic or surgical procedure, a clinician guides the endoscope or laparoscope into the desired region of the patient while viewing the video image from the device on the video display. When the endoscope or laparoscope is positioned in or pulled through the appropriate region, the surgeon or clinician may perform a procedure using instruments that may be necessary as previously discussed.

Whereas in many cases older technology boroscopes or fiberscopes would automatically maintain a known orientation when the scope was rotated (the proximal viewing end being rotated along with the distal end), clinicians may tend to lose the reference horizon when rotating a video scope. Video-based scopes have heretofore typically output an image to a (non-rotating) video monitor that is constant relative to the x-y coordinates of a (rotatable) image capture mechanism. Thus, "up" on the video monitor does not necessarily always represent "up" relative to the clinician's reference plane. To combat this effect, clinicians must typically pay close attention to exploratory movements of the tip or instruments in the field of view.

BRIEF DESCRIPTION OF THE DRAWINGS

Non-limiting and non-exhaustive embodiments of the present invention are described with reference to the following drawings.

DETAILED DESCRIPTION

Figure 1A:
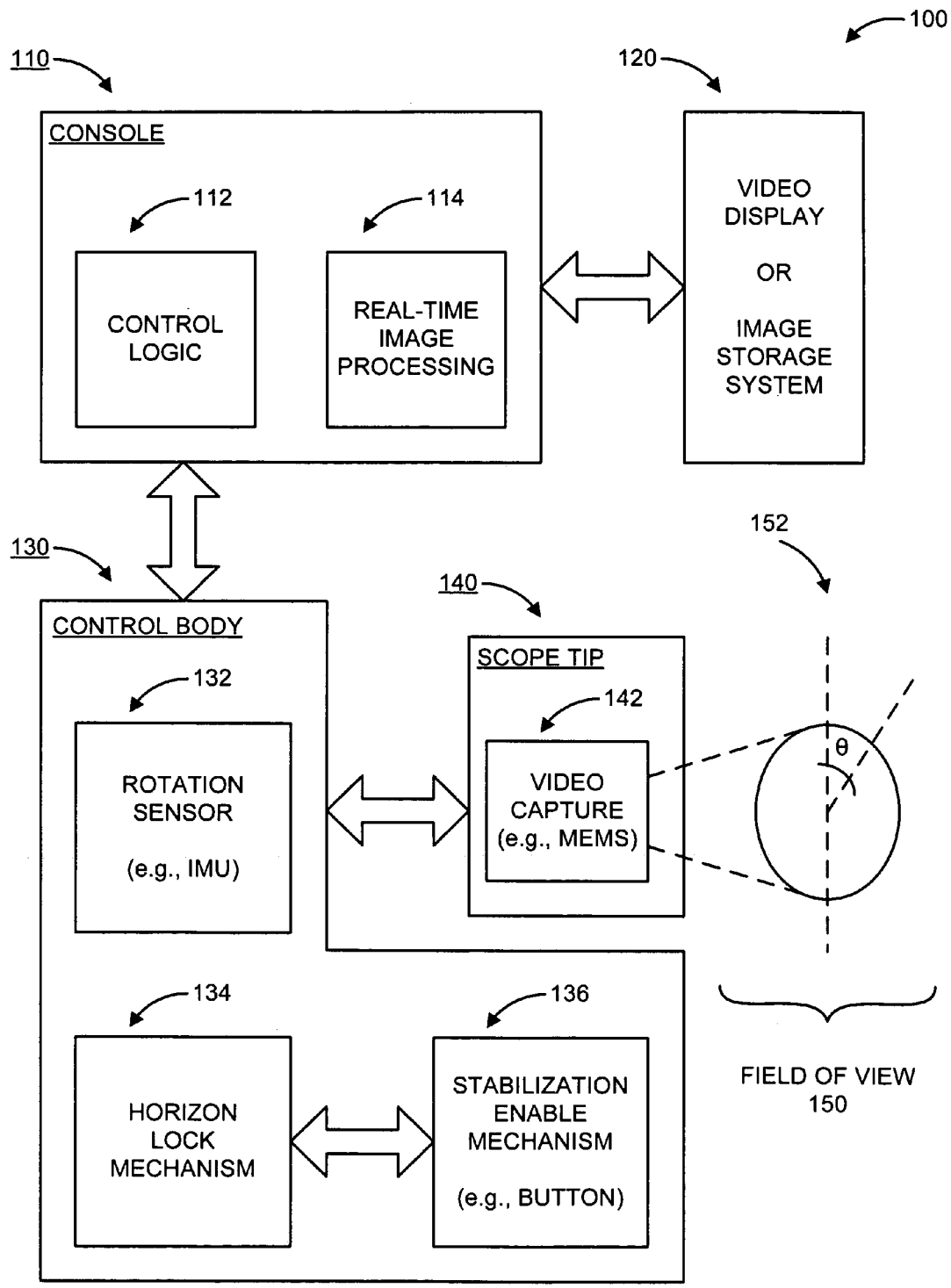
FIG. 1A is an illustrative block diagram for a system that is arranged to compensate and stabilize an image according to an embodiment.

Various embodiments will be described in detail with reference to the drawings, where like reference numerals represent like parts and assemblies throughout the several views. Reference to various embodiments does not limit the scope of the invention, which is limited only by the scope of the claims attached hereto. Additionally, examples set forth in this specification are not intended to be limiting and merely set forth some of the many possible embodiments for the claimed invention.

Briefly stated, the present disclosure is generally related to an image processing system arranged to provide rotation compensation and image stabilization in a video scope system such as in endoscopy and laparoscopy systems. According to some embodiments, the image processing functions may operate at real-time frame rates so that the resulting processed image is observable with no time lag. A rotation sensor such as an inertial measurement unit (IMU) is included in the system to sense the position of scope, and in particular, the rotation of the scope with respect to gravity. The sensed scope rotation may be used to cause rotation of the collected image and/or an image displayed on a video monitor. According to one embodiment, the sensed rotation may be used to identify or calculate a coordinate transformation matrix that is used for processing the image data. According to some embodiments, the system may include a horizon lock mechanism that can be user-actuated to engage rotation compensation. When the horizon lock mechanism is not engaged, the output image is locked to the scope tip and rotates with rotation of the scope.

According to some embodiments, when rotation compensation is enabled a coordinate transformation matrix is applied to the image data to provide a transformed image that is relatively rotation free relative to an artificial horizon.

According to other embodiments, when rotation compensation is enabled, image gathering coordinates may be adjusted to maintain a substantially constant horizon relative to the clinician. For embodiments using a focal plane sensor, such adjustment may be made for example by rotating the sensor within the tip housing. For embodiments using a scanned beam image capture system, the scanning coordinates of a video capture device may be modified, for example by varying the phase relationship of x-y actuators or by rotating the video capture device relative to the tip housing.

According to an embodiment a console is arranged to apply a rotation matrix to de-rotate image data in real-time. The console evaluates positional information that is provided from a rotation sensor, for example an inertial measurement unit, that may be included in a control body (e.g., a body of hand-tool), a body of a scope, or a body of a scope-tip. The rotation matrix is selected by the console based on the sensed positional information associated with the rotation sensor.

According to an embodiment, the system may include features to permit user selection of horizon lock via a horizon lock mechanism. Deactivation of the horizon lock mechanism unlocks the artificial horizon associated with the image data such that de-rotation is not applied. Activation of the horizon lock mechanism engages rotation compensation and substantially locks the orientation of the image relative to storage or video display devices.

According to an embodiment, the system may include a horizon set mechanism to permit user selection of a preferred reference horizon. Upon activation of the horizon set mechanism, the artificial horizon is locked according to the selected rotation. According to some embodiments, the horizon set mechanism may select the current rotation associated with the rotation sensor.

Another aspect of the present disclosure generally related to a facility that can be provided in the console drive a heads-up display such as a see-through display. A see-through display may allow display of the image data over the viewer's field of view.

According to various embodiments, displayed information may include temperature, angle of horizon, artificial horizon line, actual horizon line, and compass direction, and/or other desired data in addition to image data.

According to another aspect, the present disclosure contemplates that some sensory information from a rotation sensor may result in a singularity that could cause problems in a de-rotation of image data (e.g., a divide by zero operation). Some embodiments may include facility to detect the singularity and avoiding altering the rotation matrix in such a way that will cause problems in the de-rotation of the image data.

According to some examples, a method is provided for stabilizing and compensating image rotations by: acquiring positional information from a rotation sensor (e.g. an inertial measurement unit), acquiring image data from a scope, determining an orientation of the scope from the acquired positional information, and selecting and applying a rotation matrix to the data to provide an image that is relatively rotation free. The method may include a variety of calculation methods for updating models for rotation transformation based on the acquired data, as well as other data-logging facilities.

According to some embodiments, a one-dimensional (1D) image data stream is provided from a video capture device that is located in a body of a scope tip to observe a field of view. Pixels from the 1D image data stream are assigned to a two-dimensional (2D) location in a scan image according to a scan assignment matrix. A rotation sensor (e.g., an inertial measurement unit) is arranged to sense positional information associated with the scope. The scan assignment matrix can be dynamically selected in response to the sensed positional information such that the scan assignment matrix provides a de-rotation function. The selection of the scan assignment matrix can be made by calculating a new scan matrix, or by selecting one of a multiplicity of scan matrices that are pre-calculated.

According to some example embodiments of the present disclosure, an image capture device is located within a body of a scope tip, where the image capture device includes facility to capture 2D image data. The image capture device is arranged to communicate with a console that includes a real-time image processor. The real-time image processor is operable to de-rotate image data from the image capture device based on a position associated with the body of the scope tip.

According to some embodiments, a rotation sensor is located within a body of a control body that is coupled to a scope tip. The rotation sensor is arranged to sense positional information that is associated with the control body such that the rotational position of the scope tip is known.

According to some examples, a rotation sensor (e.g. an inertial measurement unit) is located within a body of a control body that is coupled to a scope tip. The rotation sensor is arranged to sense positional information that is associated with the control body such that the rotational position of the scope tip is known.

According to some embodiments, a rotation sensor is located within a body of a scope tip. The rotation sensor is arranged to sense positional information that is associated with the scope tip such that the rotational position of the scope tip is known.

According to other examples, a rotation sensor such as an inertial measurement unit is located within a body of a scope tip. The rotation sensor is arranged to sense positional information that is associated with the scope tip such that the rotational position of the scope tip is known.

In some embodiments, an image capture device is located within a body of a scope tip device that can be either a rigid-type scope tip or a flexible-type scope tip. Example scopes may comprise: an endoscope, a laparoscope, an encephaloscope, a laryngoscope, an esophascope, a thoracoscope, an angioscope, a nephroscope, a colonoscope, a proctoscope, an arthoscope, a rhinoscope, an esophagoscope, a brochoscope, a mediastinoscope, a gastroscopes, an amnioscope, a cystoscopes, and/or a hysteroscope, to name a few.

In some embodiments, the video capture device can include: a MEMS-type scanner, a moving fiber scanner, a CMOS-type focal plane detector, a CCD-type focal plane detector, a photo-diode type non-imaging detector, an avalanche photo-diode type non-imaging detector, a PIN photo-diode type non-imaging detector, a MEMS scanner that operates in a progressive scan pattern, a MEMS scanner that operates in a bi-sinusoidal scan pattern, an electrostatically driven MEMS scanner, a magnetically driven MEMS scanner, a piezo-electrically driven MEMS scanner, a bi-morph driven MEMS scanner, a bulk micro-machined MEMS scanner, a surface micro-machined MEMS scanner, a galvanometer, and/or a rotating polygon mirror.

The rotation sensor that is described in the present disclosure can be a device or set of devices that provide positional information for utility in the related image processing system or image capture system. Example devices that are contemplated include, but are not limited to, accelerometers, gyroscopes, inertial measurement devices, strain sensors, bubble gauges, mercury gauges, etc.

Example rotation sensing devices that may be used in some embodiments may include types such as: a piezo film type accelerometer, a piezo-electric type accelerometer, surface micro-machined capacitive MEMS type accelerometer, a bulk micro-machined capacitive type accelerometer, a bulk micro-machined piezo resistive type accelerometer, an electromechanical servo type accelerometer, a null-balance type accelerometer, a strain gauge type accelerometer, a resonance type accelerometer, a magnetic induction type accelerometer, an optical type accelerometer, and a surface acoustic wave type accelerometer.

Example rotation sensing devices that may be used in some embodiments also include: a spinning mass gyroscope, an optical gyroscope, a ring laser type gyroscope, a fiber-optic type gyroscope, a vibrating gyroscope, and a piezo-electric gyroscope.

The described embodiments, examples, features, and other desirable effects will become more apparent by way of the following examples.

Example System Diagram

FIG. 1A is an illustrative block diagram for a system (100) that is arranged to compensate and stabilize an image according to an embodiment. The system includes a console (110), a video display or image capture system (120), a control body (130) and a scope tip (140).

The console is arranged in cooperation with the video display or storage system (120) and the control body (130), while the control body (130) is arranged in cooperation with the scope tip (140). In operation, the clinician uses the control body to guide the scope into a body cavity of a patient during a diagnostic or surgical procedure. The scope tip (140) is arranged to receive image data from a field of view (150), which corresponds to the body cavity region of the patient. The image data from the scope tip (140) is communicated to the console (110). The control body (130) is arranged to sense a position associated with the scope tip (140). The sensed position is communicated to the console (110) by the control body (130). The console (110) is arranged to evaluate the sensed position associated with the scope tip (140) and provide a transformation to the image data that is appropriate for the sensed position associated with the scope tip (140). The transformed image data is formatted by the console (110) for output to an appropriate device such as, for example, video display (120) or image storage system (120).

The console (110) includes functional blocks for control logic (112) and real-time image processing (114). The control logic block (112) is arranged to provide functions associated with monitoring and processing the sensed position associated with the scope tip (140) relative to a reference. The control logic block (112) is also arranged to receive the image data from the scope tip (140), and coordinate the transfer of the image data to the real-time image processing block (114). The real-time image processing block (114) is arrange to provide a transformation to the image data based upon the sensed position information and other related controls, which are provided by control logic (112). The transformed image data is formatted for output and provided to the video display (120) or image capture system (120) by the real time image processing block (114).

Although the console (110) is illustrated with two separate functional blocks, the specific implementations of the functions may be combined in some embodiments, further separated into other functions, or other combination that is appropriate to provide the overall desired functionality of the console (110). Additional functions may also be provided by the console (110) such as power supply regulation for various circuits, amplification and/or filtering of input and output signals, control of a light source, formatting signals for communication formats, as well as others.

The image signals that are provided between the console (110) and other devices may be an appropriate signal type such as that from: a fiber optic coupling, a video signal, a serial communication port, a parallel communication port, a universal serial bus interface (USB), an IEEE 1394 (aka firewire) interface, a network connection such as Ethernet, a wireless network connection such as 802.11a/b/g, a wireless network connection such as Bluetooth, or some other type of communication connection.

In some embodiments, the console (110) is arranged to provide control and processing functions that are necessary to format video images for display on the video display (120). For such embodiments, the transformed image data is further processed to provide a video output signal that is in the format that is required by the video display (120). Contemplated video formats include appropriate video output signal such as, for example: NTSC, PAL, SECAM, VGA, SVGA, XVGA, RGB, DVI, HD, and others.

In other embodiments, the console (110) is arranged to provide a video output signal that is suitable for recording with an image storage system (120). For such embodiments, the transformed image data may be further processed to provide a data output signal that is in the format required by the image storage system (120). The image storage system (120) may, for example, be a video recording device that requires a standard video signal (see above), a hard disk drive (HDD) based recording system, or another data capture device that is arranged to receive image data from a communication port. Example communication ports that are contemplated include, but are not limited to, fiber optic communication, a serial communication port, a parallel communication port, a universal serial bus interface (USB), an IEEE 1394 (aka firewire) interface, a network connection such as Ethernet, a wireless network connection such as 802.11a/b/g, a wireless network connection such as Bluetooth, or some other type of communication connection.

The control body (130) may include functional blocks for a rotation sensor (132) such as, for example, an inertial measurement unit or IMU, a horizon lock mechanism (134), and a stabilization enable mechanism (136). For embodiments using a rotation sensor (132) in the control body (130), the rotation sensor (132) is arranged to sense a position associated with the control body (130). According to some embodiments, the coupling between the control body (130) and the scope tip (140), including the distal end of the scope tip, is relatively torsionally rigid, an arrangement that makes relative rotation sensing within the control body (130) indicative of the relative rotation of a field-of-view (150) generated at the distal end of the scope tip (140). The stabilization enable mechanism (136) is arranged for actuation by a clinician to activate horizon stabilization. The horizon lock mechanism (134) is arranged for actuation to select an image orientation as a reference horizon. For example, according to some embodiments, activation of the horizon lock mechanism (134) sets the current image orientation as the reference horizon (e.g., 152). The control body (130) is configured to communicate the sensed position from the rotation sensor (132) to the console (110) such that the sensed position of the distal end of the scope tip (140) is provided to the console (110) relative to the reference horizon.

The rotation sensor (132) may be arranged to sense the position of the scope tip (140) in some embodiments by sensing the control body (130) orientation relative to gravity. For example, the control body (130) is oriented at an angle that is relative to the local gravity. When the control body (130) is rotated, the rotation sensor (132) senses that the angle (e.g., θ) of the change. A torsionally stiff (but optionally laterally flexible) coupling between the control body (130) and the distal end of the scope tip (140) makes the relative orientation of the control body (130) indicative of the relative orientation of the distal end of the scope tip (140). The sensed change in angle is received by the console (110) and used by the control logic (112) to identify a de-rotation transformation for the image data. Alternatively, the sensed change may be used by the control logic (112) to drive a change in a video capture mechanism (142) within the distal end of the scope tip (140), driving the video capture mechanism (142) to capture an image at a desired, horizon locked orientation.

In some implementations, the control body (130) is also arranged to communicate an image lock or "lock horizon" signal from the horizon lock mechanism (134) to the console (110). In one example, the horizon lock mechanism (134) is a push button that is configured to communicate a "lock horizon" signal to the console (110), and the console (110) is arranged to evaluate the current position from the rotation sensor (132) when the lock horizon signal is asserted. The artificial horizon then corresponds to the sensed position from the rotation sensor (132) such as when the horizon is locked. Additional control logic (not shown) may be provided in the control body (130) such that the "lock horizon" signal is appropriately communicated to the console (110) according to appropriate communication signal formats.

In some other implementations, the horizon lock mechanism (134) can be a momentary switch that is configured to communicate a "lock horizon" signal to the rotation sensor (132). For this example, the rotation sensor (132) is arranged to lock a reference horizon position in the rotation sensor (132) when the "lock horizon" signal is asserted. Subsequent angular information that is communicated from the rotation sensor (132) to the console (110) is then provided as an angle relative to the selected artificial horizon. The angular information can again be formatted and/or processed for communication between the rotation sensor (132) and the console (110).

In some embodiments, the control body (130) may include functional blocks for a rotation sensor (132), and a horizon lock mechanism (134). The rotation sensor (132) is arranged to sense a position associated with the control body (130) and the scope tip (140). The horizon lock mechanism (134) is arranged for actuation by a clinician to lock the current image orientation as the reference horizon (e.g., 152). The control body (130) is configured to communicate the sensed position from the rotation sensor (132) to the console (110) such that the sensed position of the scope tip (140) is provided to the console (110) relative to the reference horizon.

Scope tip 140 can be a flexible device such as an endoscope, or a rigid device such as a laparoscope. Scope tip 140 is also illustrated with a video capture device (142) that is configured to scan the field of view (150) and communicate image data from the scanned field of view to the control body (130). In some embodiments, the video capture device (142) can be a scanner such as, for example, a MEMS scanner that operates in a progressive scan pattern or a MEMS scanner that operates in a bi-sinusoidal scan pattern. In some embodiments, the scanner may be operated by electrostatic drive, by a combination of magnetic and electrostatic drive, or other known means such as piezoelectric or bi-morph drive. An example MEMS scanner may be a bulk micro-machined scanner, a surface micro-machined device, or another type that is known in the art. The surface of the mirror on the MEMS scanner can be flat or alternatively include optical power to assist in forming a beam of an appropriate shape.

Figure 1B:
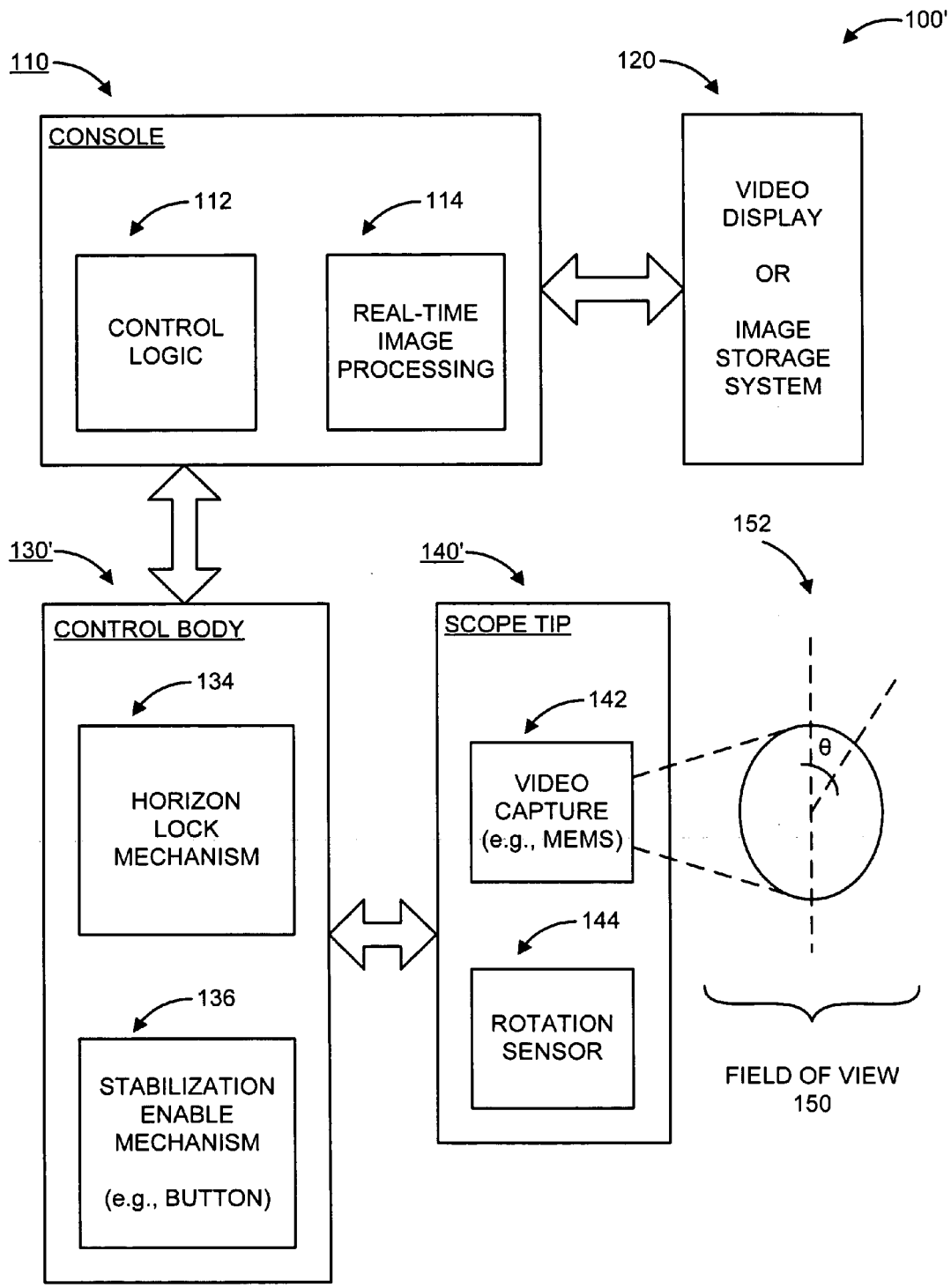
FIG. 1B is an illustrative block diagram for a system that is arranged to compensate and stabilize an image according to an embodiment.

While some of the examples described above with reference to FIG. 1A contemplate locating the rotation sensor (132) in the control body (130), the present disclosure is not so limited. In some implementation such as that illustrated, for example, by FIG. 1B, the rotation sensor (132) of FIG. 1A may be placed in the scope tip (140). As illustrated in FIG. 1B, a scope tip (140') includes a rotation sensor (144). In this example, the scope tip (140') is configured to communicate the sensed position from the rotation sensor (144) to the console (110) through the control body (130').

Although the above described examples discuss endoscopes and laparoscopes, the present disclosure is not so limited. Scope devices that are contemplated include a tubular body, which can be circular or ovular in shape, and a distal tip that is guided into a body cavity of a patient during a diagnostic or surgical procedure. The tubular body may be a rigid body such as in a laparoscope, or a flexible body such as an endoscope. A variety of specialized scopes also are contemplated such as: an encephaloscope, a laryngoscope, an esophascope, a thoracoscope, an angioscope, a nephroscope, a colonoscope, a proctoscope, an arthoscope, a rhinoscope, an esophagoscope, a brochoscope, a mediastinoscope, a gastroscopes, an amnioscope, a cystoscopes, and a hysteroscope, to name a few.

Example Scanned Beam Imager

Figure 2:
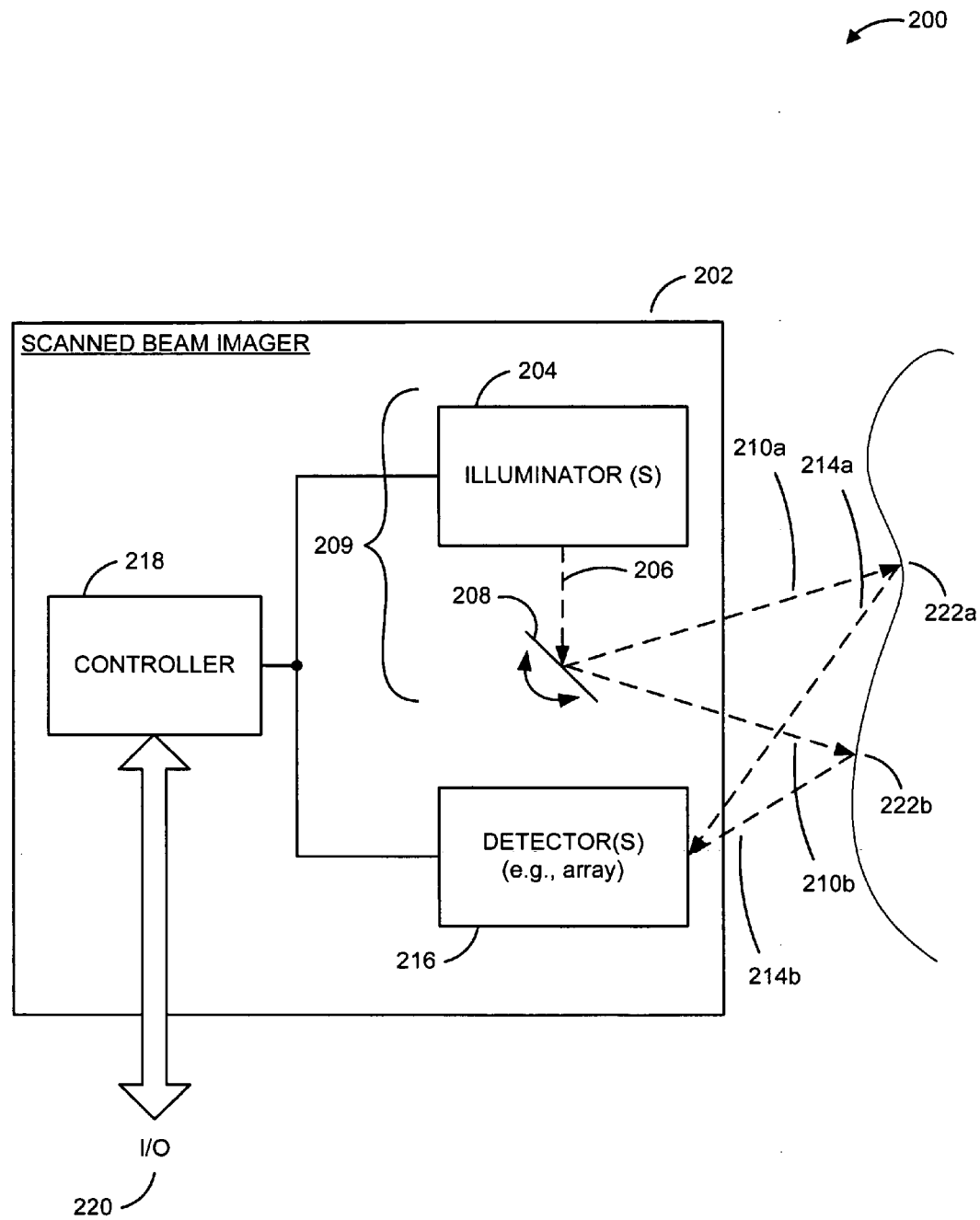
FIG. 2 shows a block diagram of a scanned beam imager, which may be used as the video capture device for FIG. 1A or FIG. 1B, according to some embodiments.

FIG. 2 shows a block diagram of a scanned beam imager 202, which may be used as the video capture device (142) for FIG. 1A or FIG. 1B, according to some embodiments.

An illuminator (204) may be arranged to create at least a first beam of light (206). A scanner (208) may be arranged to deflect the first beam of light across a field-of-view (FOV) to produce a second scanned beam of light (210), which is shown as positions 210a and 210b. The scanned beam of light (210) sequentially illuminates spots in the FOV, which is shown as positions 222a and 222b, as corresponding beam positions 210a and 210b, respectively. While the beam (210) illuminates a spot in the FOV, the illuminating light beam (210) is reflected, absorbed, scattered, refracted, or otherwise affected by the properties of the object or material to produced scattered light energy. A portion of the scattered light energy 214, shown emanating from spot positions 222a and 222b as scattered energy rays 214a and 214b, respectively, travels to one or more detectors (216) that are arranged to receive the light and produce electrical signals corresponding to the amount of light energy received. The electrical signals drive a controller (218) that builds up a digital image and transmits it for further processing, decoding, archiving, printing, display, or other treatment or use via interface 220.

Illuminator 204 may include multiple light emitters such as, for instance, light emitting diodes (LEDs), lasers, laser diodes, thermal sources, arc sources, fluorescent sources, gas discharge sources, or other types of illuminators. In some embodiments, illuminator 204 comprises a red laser diode having a wavelength of approximately 635 to 670 nanometers (nm). In other embodiments, illuminator 204 comprises three lasers; a red diode laser, a green diode-pumped solid state (DPSS) laser, and a blue DPSS laser at approximately 635 nm, 532 nm, and 473 nm, respectively. While laser diodes may be directly modulated, DPSS lasers may generally require external modulation such as an acousto-optic modulator (AOM) for instance. For externally modulated lasers, the external modulator may be considered part of illuminator (204).

Illuminator 204 may include, such as in the case of multiple emitters, beam combining optics to combine at least some of the emitters into a single beam. Light source 204 may also include beam-shaping optics such as one or more collimating lenses and/or apertures. Additionally, while the wavelengths described in the previous embodiments have been in the optically visible range, other wavelengths may be within the scope of the invention. Light beam 206, while illustrated as a single beam, may comprise a plurality of beams converging on a single scanner 208 or onto separate scanners 208.

The Example MEMS scanners that may be used for scope applications are described, for example, in U.S. Pat. No. 6,140,979, entitled SCANNED DISPLAY WITH PINCH, TIMING, AND DISTORTION CORRECTION; U.S. Pat. No. 6,245,590, entitled FREQUENCY TUNABLE RESONANT SCANNER AND METHOD OF MAKING; U.S. Pat. No. 6,285,489, entitled FREQUENCY TUNABLE RESONANT SCANNER WITH AUXILIARY ARMS; U.S. Pat. No. 6,331,909, entitled FREQUENCY TUNABLE RESONANT SCANNER; U.S. Pat. No. 6,362,912, entitled SCANNED IMAGING APPARATUS WITH SWITCHED FEEDS; U.S. Pat. No. 6,384,406, entitled ACTIVE TUNING OF A TORSIONAL RESONANT STRUCTURE; U.S. Pat. No. 6,433,907, entitled SCANNED DISPLAY WITH PLURALITY OF SCANNING ASSEMBLIES; U.S. Pat. No. 6,512,622, entitled ACTIVE TUNING OF A TORSIONAL RESONANT STRUCTURE; U.S. Pat. No. 6,515,278, entitled FREQUENCY TUNABLE RESONANT SCANNER AND METHOD OF MAKING; U.S. Pat. No. 6,515,781, entitled, SCANNED IMAGING APPARATUS WITH SWITCHED FEEDS; and U.S. Pat. No. 6,525,310, entitled FREQUENCY TUNABLE RESONANT SCANNER, each being commonly assigned herewith, and all hereby incorporated by reference.

An example scanner (208) may be a 2D MEMS scanner 208 arranged to scan one or more light beams at high speed in a pattern that covers an entire 2D FOV or a selected region of a 2D FOV within a frame period. A typical frame rate may be 60 Hz, for example. Often, it is advantageous to run one or both scan axes resonantly. In one embodiment, one axis is run resonantly at about 19 KHz while the other axis is run non-resonantly in a sawtooth pattern so as to create a progressive scan pattern. A progressively scanned bi-directional approach with a single beam scanning horizontally with a scan frequency of approximately 19 KHz and scanning vertically in sawtooth pattern at 60 Hz can approximate an SVGA resolution. In example system, the horizontal scan motion is driven electrostatically and the vertical scan motion is driven magnetically. In another example system, both the horizontal and vertical scan may be driven magnetically or capacitively. Electrostatic driving may include electrostatic plates, comb drives or similar approaches. In various embodiments, both axes may be driven sinusoidally or resonantly.

A selection of the detector (216) depends upon the application or desired configuration. For example, in one embodiment, the detector may include a simple PIN photodiode connected to an amplifier and digitizer. In this example configuration, beam position information may be retrieved from the scanner or, alternatively, from optical mechanisms, and image resolution is determined by the size and shape of scanning spot 212. In the case of multi-color imaging, the detector (216) may comprise more sophisticated splitting and filtering to separate the scattered light into its component parts prior to detection. As alternatives to PIN photodiodes, avalanche photodiodes (APDs) or photomultiplier tubes (PMTs) may be preferred for certain applications, particularly low light applications.

In various approaches, simple photodetectors such as PIN photodiodes, APDs, and PMTs may be arranged to stare at the entire FOV, stare at a portion of the FOV, collect light retrocollectively, or collect light confocally, depending upon the application. In some embodiments, the photodetector (216) may be arranged to collect light through filters to eliminate much of the ambient light.

The present device may be embodied as monochrome, as full-color, and even as a hyper-spectral. In some embodiments, it may also be desirable to add color channels between the conventional RGB channels used for many color cameras. Herein, the term grayscale and related discussion shall be understood to refer to these embodiments as well as other methods or applications within the scope of the invention. In the control apparatus and methods described below, pixel gray levels may comprise a single value in the case of a monochrome system, or may comprise an RGB triad or greater in the case of color or hyperspectral systems. Control may be applied individually to the output power of particular channels (for instance red, green, and blue channels), may be applied universally to the channels, or may be applied to a subset of the channels.

In some embodiments, the illuminator may emit a polarized beam of light or a separate polarizer (not shown) may be used to polarize the beam. In such cases, the detector (216) may include a polarizer cross-polarized to the scanning beam (210). Such an arrangement may help to improve image quality by reducing the impact of specular reflections on the image.

In some approaches a solid-state pixelated sensor array can be used as the detector. Example pixilated sensor arrays include a charge-coupled device (CCD) and a complementary metal-oxide semiconductor (CMOS) device. The pixilated sensor array may consist of an array of light-sensitive elements that develop an electrical charge when exposed. Additional optical filters, optical lenses, and other optical processing elements may be used in cooperation with the pixilated sensor array to provide a desired image.

The detector (216) may also include an analog-to-digital converter (ADC) that outputs the electrical signal from the sensor array, or other sensor elements, as a digitally encoded signal (e.g., binary value). The controller (218) may also be arranged to provide data formatting and other signal processing functions to the image data that is generated from the detector (216).

Example Video Scope System Environment

Figure 3:
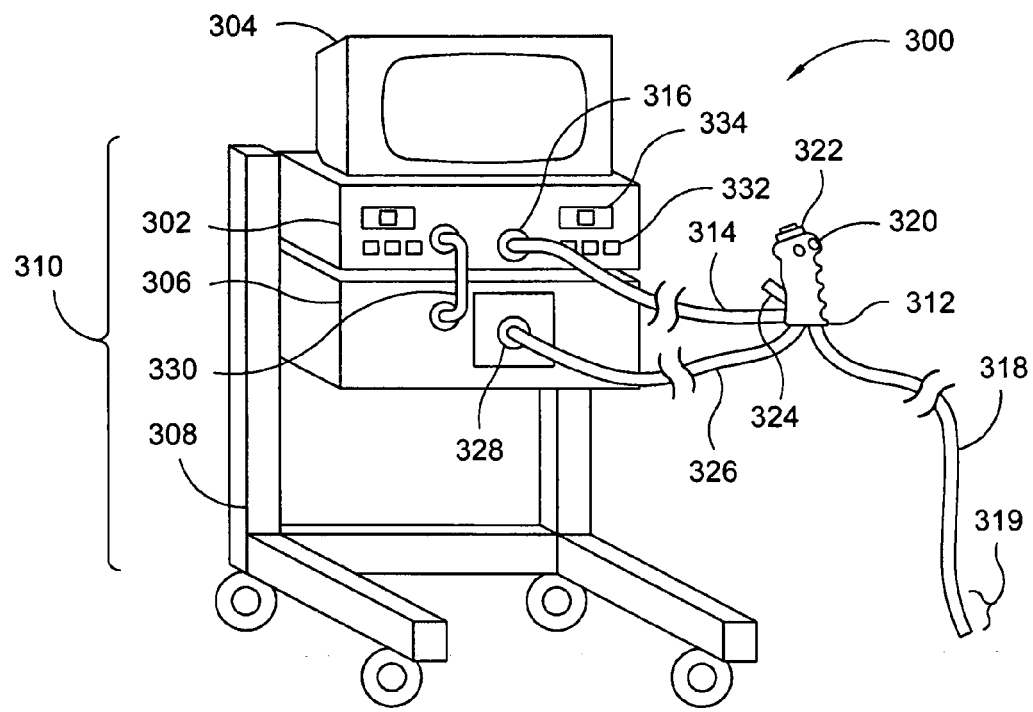
FIG. 3 is an isometric drawing of a video scope system such as an endoscopy system according to an embodiment.

FIG. 3 is an isometric drawing of a video scope system (300) such as an endoscopy system, according to at least one embodiment. System 300 includes a control module (302), a monitor (304), and an optional pump (306) which may be mounted on a cart (308). Taken together, the described modules may be referred to as a console (310).

Items comprising console 310 may optionally be mounted separately or may be combined as appropriate for the application. Console 310 can arranged in communication with a control body (e.g., a hand piece) 312 through an external cable (314), which can be connected to console 310 via connector 316. Connector 316 has two parts (316a and 316b, not shown for clarity) that may be selectively coupled together, or decoupled from one another. Control body 312 is connected to a scope (318), which may be of a flexible type scope (e.g., an endoscope) or a rigid type scope (e.g., a laparoscope). A distal scope tip (319), which may for example be a steerable tip, includes means for scanning a beam over a field-of-view, collecting the scattered light energy, and sending a signal representative of the collected light energy back up through scope 318, control body 312, and external cable 314 into console 310.

Control body 312 may include optional controls 320, which may for example include brightness, zoom, still photo, FOV angle, tip wash, irrigate, lubricant dispense, and other inputs that are advantageous to have immediately accessible to the user. Additionally, when scope 318 is of a flexible type, control body 312 may include steering controls 322 that control the angle that the distal scope tip (319) makes with respect to the rest of scope 318. Control body 312 may further include working channel fitting 324, into which may be inserted various tools that may be threaded down the working channel of scope 318, and emerging substantially at the end of the distal scope tip (319) to perform various surgical, diagnostic, or other tasks.

Optional pump 306 may include a separate irrigation hose (326) that connects to control body 312. Irrigation hose 326 may be connected to optional pump 306 via connector 328. Solution pumped through irrigation hose 326 is from there forced into the optional irrigation channel of scope 318. Alternatively, optional pump 306 may include a shunt hose (330) that connects to control module 302, fluids carried by shunt hose 330 thereafter being combined with other signal lines within control module 302 to be sent to the control body 312 and on to scope 318 via connector 316 and external cable 314. This optional arrangement results in fewer external hoses and cables to get in the way of the user.

As an alternative or in addition to pump 306, suction may be applied for removing unwanted fluids and debris from the working space.

Console 310 may also include additional controls 332 and/or indicators 334, here shown as being on control module 302. These controls and indicators may, for example, be useful when setting up or troubleshooting the apparatus of FIG. 3.

Figure 4:
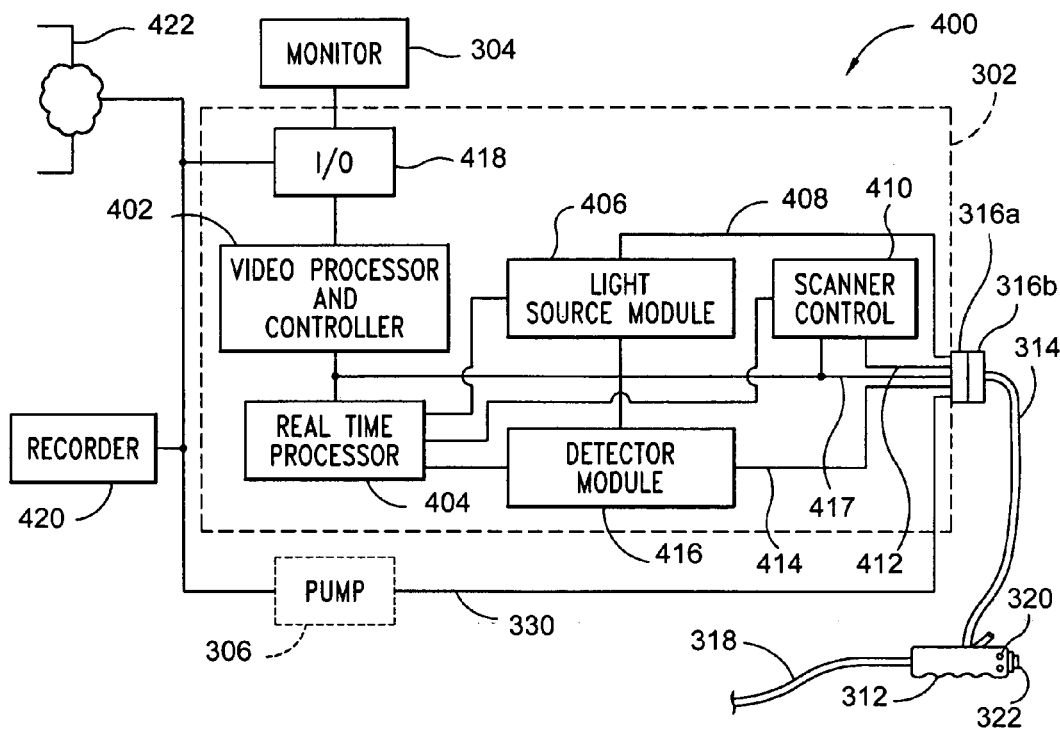
FIG. 4 is a block diagram emphasizing relationships between various components of an endoscope system such as illustrated in FIG. 3 according to an embodiment.

FIG. 4 is a block diagram (400) emphasizing relationships between various components of a scope system such as illustrated in FIG. 3, according to an embodiment. Control module 302 contains several logical and/or physical elements that cooperate produce an image on monitor 304. Video processor and controller 402, which may be in the form of a microcomputer main board, is arranged to receive control inputs and controls the operation modes of the other elements within control module 302. Additionally, video processor and controller 402 may include image processing functions.

Real time processor 404, which may for example be embodied as a PCI board mounted on video processor and controller 402, may alternatively be a logical device that is physically one with video processor and controller 402. Real time processor 404 interacts with light source module 406, scanner control module 410, and detector module 416. Light source module 406, which may alternatively be housed separately, includes one or more illuminators that create the light energy used for beam scanning by the imaging tip. Light source module 406 outputs light energy via optical fiber 408, which, in turn, connects to external cable 314 via connector 316, here depicted as having two sections 316a and 316b. After passing through the control body (312) en route to the scope (318) and being scanned across the FOV, light is collected at the scope tip and a representative signal returned back up through the scope (318), control body (312), and external cable 314, through connector 316 and back into the controller module 302.

In some embodiments, the representative signal passed back up through the external apparatus is sent as an optical signal. Thus return signal line 414 may be a fiber optic cable or bundle of fiber optic cables that are routed to detector module 416. At detector module 416, the optical signals corresponding to the FOV characteristics are converted into electrical signals and returned to the real time processor 404 for real time processing that includes the necessary rotational or other image transformations. The transformed image is then parsed for communication to the video processor and controller 402. Electrical signals representative of the optical signals may be amplified and optionally digitized by the detector module 416 prior to transmission to real time processor 404. Alternatively, analog signals may be passed to real time processor 404 and analog-to-digital conversion performed there. Detector module 416 and real time processor 404 may be combined into a single physical element.

In alternative embodiments, light representative of the FOV may be converted into electrical signals at the tip by one or more photo-detectors such as photodiodes, for example. In this case, return line 414 may be embodied as electrical wires and detector module 416 may be omitted. In the case where distal optical to electrical conversion is performed, it may be advantageous to amplify the detected signals in the imaging tip as well to reduce impedance, reduce electrical noise, and improve the responsivity of the detector or detectors.

Additionally, it may be desirable to perform analog-to-digital conversion at the distal scope tip (319), or alternatively in the control body (312) in the interest of reducing impedance of the relatively long signal lines that pass through external cable 314, hand piece 312, and in the case of distal tip A/D conversion, scope 318. In this case signal lines 414 may comprise digital lines and connector 316 a connector for coupling at least certain digital signals. Real time processor 404 may optionally perform signal leveling by modulating light source module output in response to the apparent brightness of the spot in the FOV.

Scanner control module 410 controls the beam scanner in the imaging tip. In the case of a scanner having integral position sensing, it may also process sense lines indicative of scanner position. Thus scanner control lines 412 may include bidirectional control lines. Scanner control module 410 may directly provide scanner drive current. Alternatively, it may provide a signal representative of desired scanner drive with conversion to drive current being performed at a more distal region such as the control body 312 or distal scope tip 319. In this case as well as other alternatives, it may be desirable to provide DC or AC power from console 310 through connector 316 and into the distal assembly.

As an alternative or adjunct to determining scanner position from scanner control lines 412, it may be advantageous to determine scanner position from the FOV representative signal passing through return signal lines 414. In this case, real time processor 404 may drive scanner control module 410 in a manner responsive to the received optical signal.

The scanner may be driven from control module 302, or alternatively the system may use the actual scanner frequency to drive the system, colloquially referred to as "tail-wags-dog".

Additionally, control lines 417 may be passed to control body 312 for input of control signals via user operation of controls 320 and optional steering controllers 322. When steering is performed under console control rather than strictly from a physical connection between steering controllers 322 and control wires, control lines 417 may additionally carry control signals outbound to control steering means. Control lines 417 may additionally carry indicator or display information to the control body 312 for transmission to the user.

Video processor and controller 402 have an interface 418 that may comprise several separate input/output lines. A video output may run to monitor 304. A recording device 420 may be connected to capture video information recording a procedure. Additionally, video scope imaging system 300 may be connected to a network (either wired or wireless) or to the Internet 422 for remote expert input, remote viewing, archiving, library retrieval, etc. Video processor and controller 402 may optionally combine data received via I/O 418 with image data and drive monitor 304 with information derived from a plurality of sources including distal scope tip 319.

In addition to or as an alternative to monitor 304, the display may be output on one or more remote devices such as, for example, a head mounted display. In that event, context information such as viewing perspective may be combined with FOV and/or other information in video processor and controller 402 to create context-sensitive information display.

In still a further example, video processor and controller 402 can be arranged to provide a heads-up display that is superimposed over the image data so that the resulting video image includes a useful indication of various data such as: temperature, angle of horizon, artificial horizon line, actual horizon line, compass direction, as well as other useful information. The heads-up display may also be configured to assist in location of the necessary tools used during a surgical or diagnostic procedure.

Pump 306 may have its control lines fed from control body 312 through control module 302. FIG. 4 illustrates the case where irrigation is run into the control module via irrigation shunt 330 and out through connector 316.

Not shown are additional optional features such as a lubricant, saline, and/or anesthetic pump.

Figure 5:
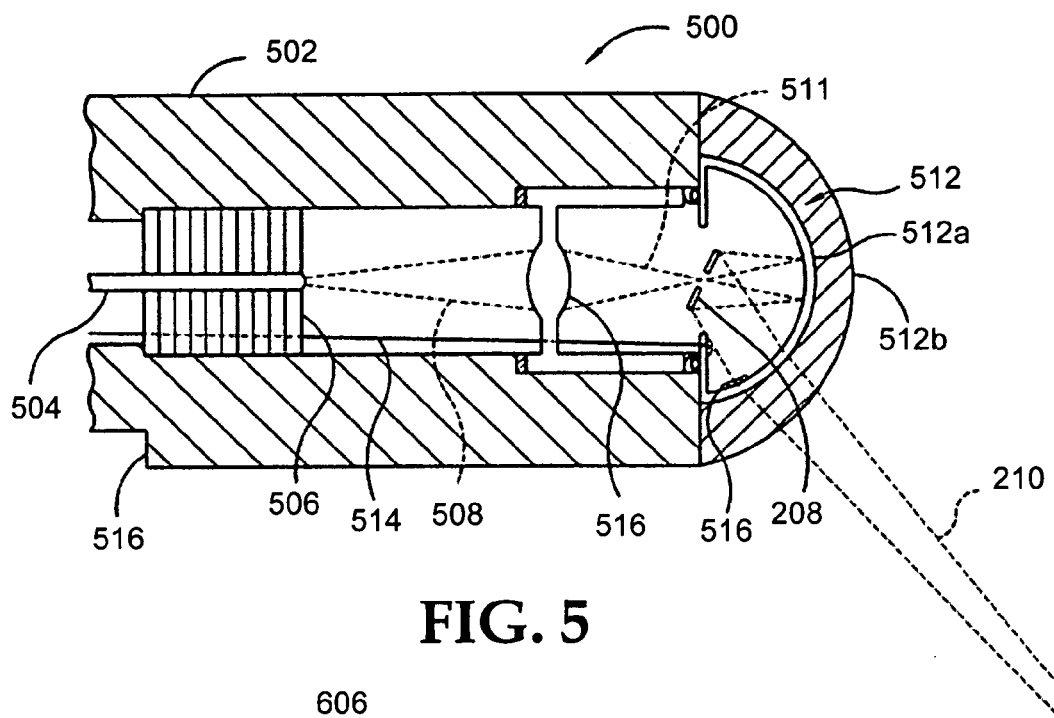
FIG. 5 is a side sectional view of a scanning module according to an embodiment.

FIG. 5 is a side sectional view of a scanning module 500, arranged according to an embodiment. The scanning module (500) is comprised of a housing 502 that encloses and supports the scanner 208 from FIG. 2 and associated mechanism. Optical fiber 504, which may for example be a single mode optical fiber feeds light to the scanning module and is affixed to housing 502 by a ferrule 506. The end of optical fiber 504 may be polished to create a known divergence angle of raw beam 508. Raw beam 508 is shaped by beam shaping optic 510 to create a beam shape appropriate for transmission through the rest of the system. As shown, at least a portion of beam shaping optic 510 may be moveable or deformable to control beam divergence, waist position, and waist angle. After shaping, shaped beam 511 is fed through an aperture in the center of the scanner 208, is reflected off a first reflecting surface back onto the front of the scanner, and then out of the scanning module as scanned beam 210.

As an alternative to or in addition to beam shaping optic 510, a reflective beam shaping optical element, optionally combined with the scan mirror 208, may be used. Such a device is taught in U.S. patent application Ser. No. 09/400, 350, entitled OPTICAL SCANNING SYSTEM WITH CORRECTION, filed Sep. 11, 2000 by Clarence T. Tegreene and David Dickensheets, commonly assigned herewith and hereby incorporated by reference.

In some embodiments of FIG. 5, a dome 512 is affixed to the end of housing 502. Dome 512 provides a number of functions. The inside of dome 512 includes the first reflecting surface, here shown as integral to the entire inside of the dome. Alternatively, the first reflecting surface may be suspended between the dome and scanner or the first reflecting surface may be formed as a specific feature of the dome such as a protruding pillar with reflective end. As shown, the inside surface of the dome provides the first reflecting surface. Additionally, the inside and/or outside of the dome may have optical power and thus further shape the beam as it passes through to become scanning beam 210. Additionally, dome 512 may provide a hermetic seal with housing 502, thus protecting optical elements inside from contact with the environment.

Control and/or power leads 514 pass through ferrule 506. Leads 514 connect to scanner 208, providing the drive signal and, optionally, position feedback. Mirror position may be determined using doped piezo-resistive elements as described in one or more of the MEMS scanner patents incorporated by reference. Electrical leads 514 may also include control and feedback connections for controlling focus characteristics of beam shaping optic 510.

Alternatively, mirror position may be determined optically. Sensing element 516 may for instance be used to detect one or more ends of scan, thus providing synchronization information. Sensing element 516 may for example be a photodiode that sends a signal to the console 310, and specifically to scanner control module 410, when it is struck by scanned beam 210. Alternatively, sensing element 516 may be an optical element of known reflectivity that sends a retro-collected optical signal back up the beam path and through optical fiber 504. In this case, a beam-splitter, evanescent coupler, or equivalent element may be incorporated in light source module 406 to pick off the returned signal for detection and transmission to other control elements such as real time processor 404.

Registration notch 516 may be formed in housing 502 to aid in registering scanning module 501 to scanning tip 319.

Figure 6:
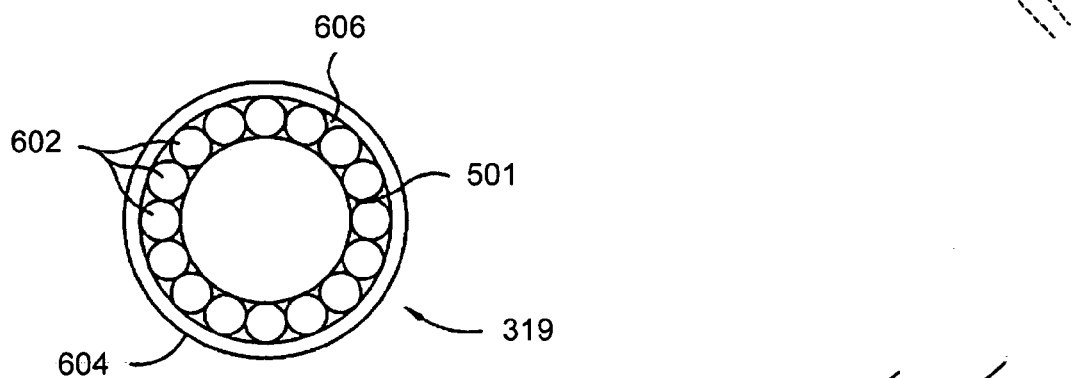
FIG. 6 is a cross sectional view of a scanning endoscope distal imaging tip according to an embodiment.

FIG. 6 is a cross sectional view of a scanning endoscope distal imaging tip 319, according to an embodiment. Scanning module 501 is surrounded by detector elements 602, which are in turn surrounded by outer sheath 604. Detector elements 602 may for example be multi-mode optical fibers that transmit the reflected signal back up distal tip 318 and on to detector module 416 in controller 302. Interstitial spaces 606 may be present among detector elements 602.

As an alternative to fiber optics, detector elements 602 may comprise optical-to-electrical converters such as photodiodes, for example. Outer sheath 604 may be flexible in the case of a flexible endoscope or alternatively may be rigid in the case of a rigid laparoscope or equivalent rigid device. As an alternative, outer sheath 604 may be inserted into another body that acts as the actual outer covering of the device.

Figure 7:
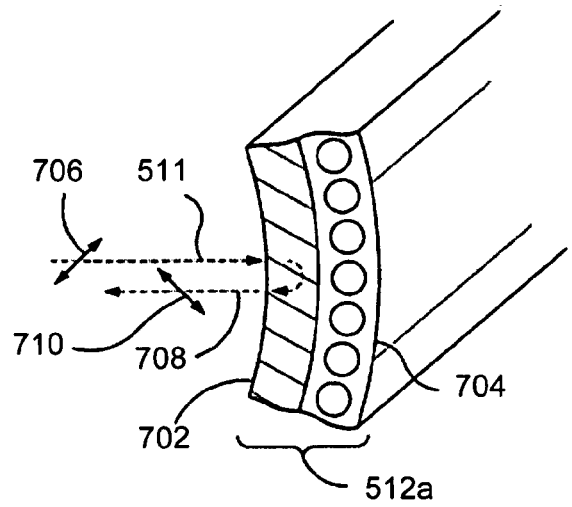
FIG. 7 is a side sectional view of an embodiment of an inside dome surface of a scanning tip module having differential reflection of two polarizations of light according to an embodiment.

FIG. 7 is a side sectional view of an embodiment of an inside dome surface of a scanning tip module having differential reflection of two polarizations of light, according to an embodiment. Inner surface 512a may be comprised of two layers, a quarter wave rotator 702, and a reflective polarizer 704. Reflective polarizers often include sub-wavelength spaced parallel conductors that allow the polarization parallel to their orientation to pass while reflecting the polarization component perpendicular to their orientation. An example of such a polarizer is disclosed in U.S. Pat. No. 6,449,092, entitled REFLECTIVE POLARIZERS HAVING EXTENDED RED BAND EDGE FOR REDUCED OFF AXIS COLOR, hereby incorporated by reference.

When incident shaped beam 511, having a particular polarization 706 passes through quarter wave plate 702, the polarization of the beam is rotated 45°. In a preferred embodiment, it is rotated to be perpendicular to the transmissive axis of reflective polarizer 704. It thus is reflected back as beam 708 through quarter wave plate 702, rotating its polarization another 45° to a polarization 710 perpendicular to incident polarization 706. Reflected beam 708 then reflects off scanner 208 (not shown), becoming scanning beam 210.

Reflective polarizer 704 may cover only a portion of the inside of dome 512 corresponding with incident light from beam 511. Alternatively, the entire inside of the dome may be covered with reflective polarizer 704. For those cases where scanning beam 110 again encounters reflective polarizer 704, it first has its polarization rotated 45° as it passes through quarter wave plate 702 a third time. This time, the polarization of scanning beam 210 is rotated to be parallel to the transmissive axis of reflective polarizer 704, and thus passes through dome 512.

As mentioned above, a semi-transparent mirror may be substituted for the reflective polarizer and other polarization-related structures.

Coordinate Transformations for Scope Applications

The presently described video scope systems are arranged to map three-dimensional (3D) coordinate spaces (x,y,z) to a two-dimensional (2D) coordinates space (x,y). An object in 3D space has a position that is described by the 3D coordinate of the object relative to some fixed reference or "origin". The orientation of the objects in the field of view for the 3D space are defined the by the objects' rotational orientation relative to one of the coordinate axis (e.g., the x-axis). The rotational orientation can be described in terms of roll, pitch, and yaw.

Conversion between a 3D coordinate system and a 2D coordinate system are performed by the real-time image processing function block (114) that is described with reference to at least FIG. 1A. The 3D image data from the FOV is multiplied by a transformation matrix that maps the 3D representation into a 2D plane. The 2D plane corresponds to a projection of the 3D object or scene onto an interposing "image" plane along the line of sight from an observer of the object.

Figures 8A, 8B:
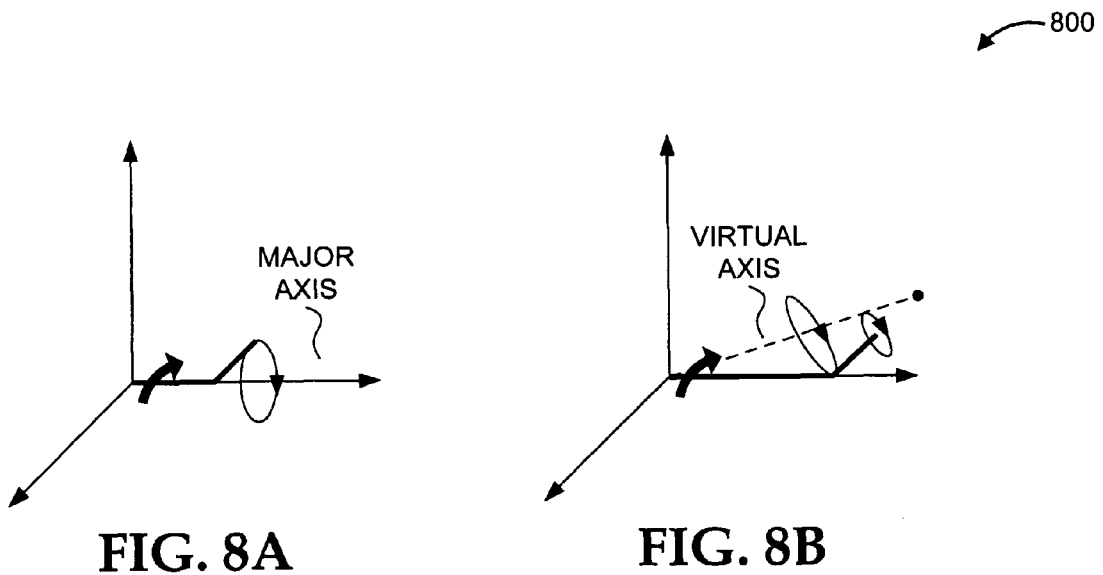
FIGS. 8A-8C illustrates various rotational aspects of a scope device according to an embodiment.
Figure 8C:
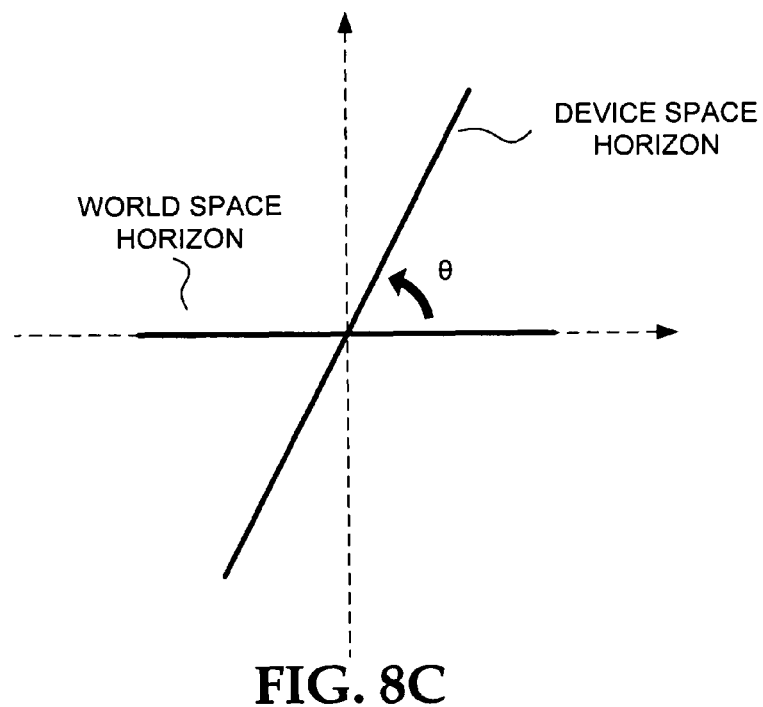

In video scope systems, the line of sight is generally perpendicular to the major axis of the objective lens. FIG. 8A illustrates a general articulating scope (e.g., an endoscope) where the scope tip is aligned along a major axis, with an arbitrary articulation angle defined as a rotation angle about the major axis. FIG. 8B illustrates that a scope tip can experience a complex motion whereby a single point in the object/scene is maintained spatially invariant in the 2D representation. FIG. 8C illustrates the concept of the concept of world and device space horizons that may result after a transformation of the image is performed.

In the case of FIG. 8A, the presently described image processing system maintains a constant horizon reference (World Space Horizon) even though the scene is constantly varying about the major axis. The described real-time image processing in this instance is arranged to examine the path of the objective lens for a simple rotation about the major axis, where the device space horizon will also rotate with respect to the World Space Horizon.

In the case of FIG. 8B, the presently described image processing system is arranged to maintain a horizon reference (World Space Horizon) in a scene whose common centroid is constant. The described real-time image processing system is arranged to examine the path of the objective lens under a complex rotation, where the Device Space Horizon will rotate with respect to the World Space Horizon. Geometric distortions may also occur in the image as a result of the complex rotation due to the precession of the objective lens' optical axis about a virtual axis that is drawn from the object in the scene to a spatially invariant point such as illustrated in FIG. 8B.

The two types of motion that are presented with respect to FIG. 8A and FIG. 8B may also occur simultaneously, where the scope tip is rotating about a major axis, and where the centroid of the scene is constant as the scope rotates about a virtual axis. The presently described system and method utilizes a combination of sensor technology and algorithmic processing to determine the nature of the rotation and translation associated with the scope tip, and to compute appropriate coordinate transformation matrices such that 3D image data can be mapped into a 2D space where a corrected image is presented without significant rotation and movement. The real-time image processing functions are required to operate with processing speeds that are appropriate for video frame rates such as, for example, 30 frames/second for NTSQ signals, such that a stable, smooth image display is available to the clinician.

An appropriate implementation for an imaging array can be used in the scope tip including but not limited to those imaging array and video capture devices previously described above. The scope can be implemented as an endoscope, a laparascope, as well as other types of scopes that use a video capture device such as an imaging array, imaging sensor, scanning imager, etc. As previously discussed, various types of data output formats and/or display formats are considered within the scope of the present disclosure. Moreover, a variety of possible communication methods between the particular constituent parts are also contemplated.

Example Block Diagram

Figure 9:
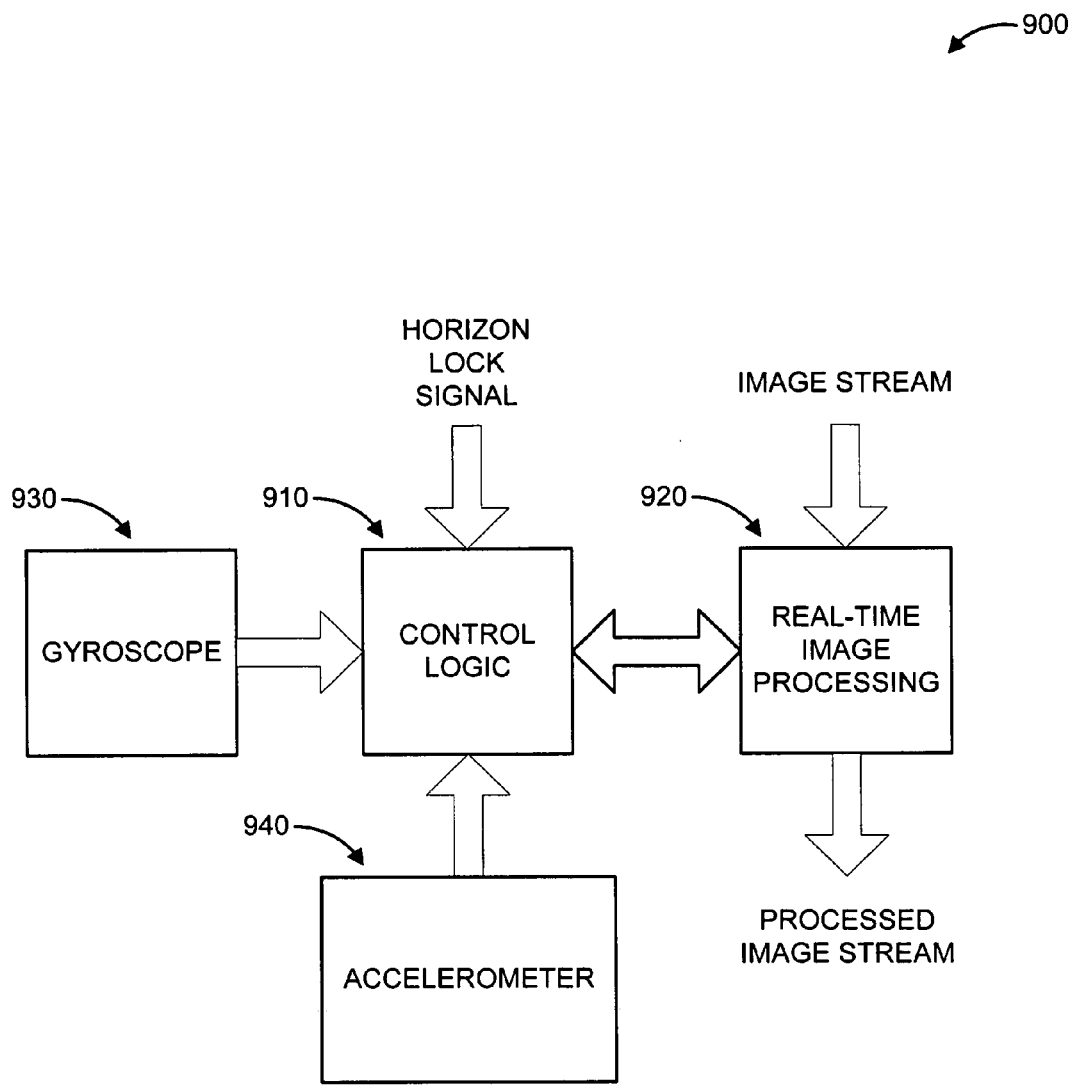
FIG. 9 is another illustrative block diagram for a system that is arranged to compensate and stabilize an image according to an embodiment.

FIG. 9 is another illustrative block diagram for a system (900) that is arranged to compensate and stabilize an image, according to an embodiment. System 900 includes a control logic block (910), a real-time image processing block (920), at least one gyroscope (930), and at least one accelerometer (940). Control logic block 910 is arranged in communication with real-time image processing block 920, gyroscope 930, and accelerometer 940.

Gyroscope 930 can be used to sense an orientation associated with the scope tip. The resulting orientation measurement signal can be either a digital signal or an analog signal. A gyroscope is a device that is based upon the concept of conservation of angular momentum, where a wheel that is spinning about an axis tends to resists changes to its orientation due to the angular momentum of the wheel. The gyro is placed on a set of gimbals so that it can continue to rotate along the same axis regardless of the motion of the scope. A set of sensors on the gimbals detect movement of the scope, where the gyroscope is mounted. The gyroscope (930) may internally include necessary signal conditioning circuitry, or provide such signal conditioning circuitry external to the accelerometer. Gyroscopes are available in numerous varieties, including but not limited to: spinning mass gyroscopes, optical gyroscopes such as ring laser and fiber optic types, vibrating gyroscopes such as piezo-electric, as well as others.

Accelerometer 940 can be used to sense motion associated with the scope tip. The resulting motion measurement signal can be either a digital signal or an analog signal. An accelerometer is an electromechanical device that will measure acceleration forces. These forces may be static, like the constant force of gravity pulling at your feet, or they could be dynamic such as those forces caused by moving or vibrating the accelerometer. By measuring the amount of static acceleration due to gravity, you can find out the angle that the accelerometer is tilted with respect to the earth. By sensing the amount of dynamic acceleration, you can analyze the way the device is moving. The accelerometer (940) may internally include necessary signal conditioning circuitry, or provide such signal conditioning circuitry external to the accelerometer. Accelerometers are available in numerous varieties, including but not limited to: piezo films, piezo-electric, surface micro-machined capacitive MEMS, bulk micro-machined capacitive, bulk micro-machined piezo resistive, electromechanical servo, null-balance, strain gauge, resonance, magnetic induction, optical, and surface acoustic wave (SAW), to name a few.

In some embodiments, the scope may contain a rotation sensor such as an inertial measurement unit (IMU) that may include one or more miniaturized gyroscope elements that are configured to provide a constant indication of the scope's roll, pitch and yaw. These values (e.g., roll, pitch and yaw) make-up an "Attitude Matrix" that is associated with the scope tip. The rotation sensor may also contain one or more miniaturized accelerometers that provide a constant indication of the instantaneous acceleration in x, y and z (device coordinates reference) that are transmitted in an "Acceleration Matrix".

Since initial placement of the scope tip is not guaranteed to provide alignment of the "Device Horizon" with the desired "World Horizon", a user control (e.g., a "Horizon Lock" signal such as discussed in FIG. 1) is provided to instantly alter the zero reference angle of the "World Horizon" and to align it with the "Device Horizon". The horizon lock mechanism can be embodied in a simple push-type button that releases the "Horizon Lock" when engaged. While the control is engaged, the Device and World Horizons are forced to align to one another such that the resulting display image will rotate with movement of the scope. When the horizon lock is engaged (e.g., release of the push button), the current World Horizon can be fixed and the rotation correction methods can be engaged such that the resulting image will not rotate if the scope tip is rotated.

According to an embodiment, the control logic block (910) is configured to accept data for the Acceleration Matrix and the Attitude Matrix from the gyroscope(s) and the accelerometer, and performs a number of mathematical computations to identify an appropriate "Rotation Matrix". The "Rotation Matrix" provides the rotation, scaling and geometric distortion correction coefficients required to convert the image stream (e.g., 2D image data from the scope) to the processed image stream (e.g., a 2D image data). The real-time image processing block (920) may be arranged to provide the processing to the image stream utilizing the rotation matrix that is identified by the control logic (910). Application of the "Rotation Matrix" to the image stream by the real-time image processing block (920) will correct for differences between the "Device Horizon" and the "World Horizon" by providing an appropriate transformation to the image data.

The image stream may contain a larger number of pixels than is required for output to the display device (e.g., NTSC, PAL, SECAM, etc.). For example, a commonly used image array may provide an image of 1280 by 1024 pixels to accommodate an output image of 640 by 480 pixels.

Although the above-described control logic block (910) is illustrated as a separate block from the real time image processing block (920), the system is not so limited. In some embodiments, the functions of the control logic block (910) and the real-time image processing block (920) may be combined together into a single functional block. Moreover, in other embodiments, the functions of either the control logic block (910) or the real-time image processing block (920) may be further broken into smaller functional blocks as may be desired in a particular implementation.

Example Image Processing Flow

Figure 10:
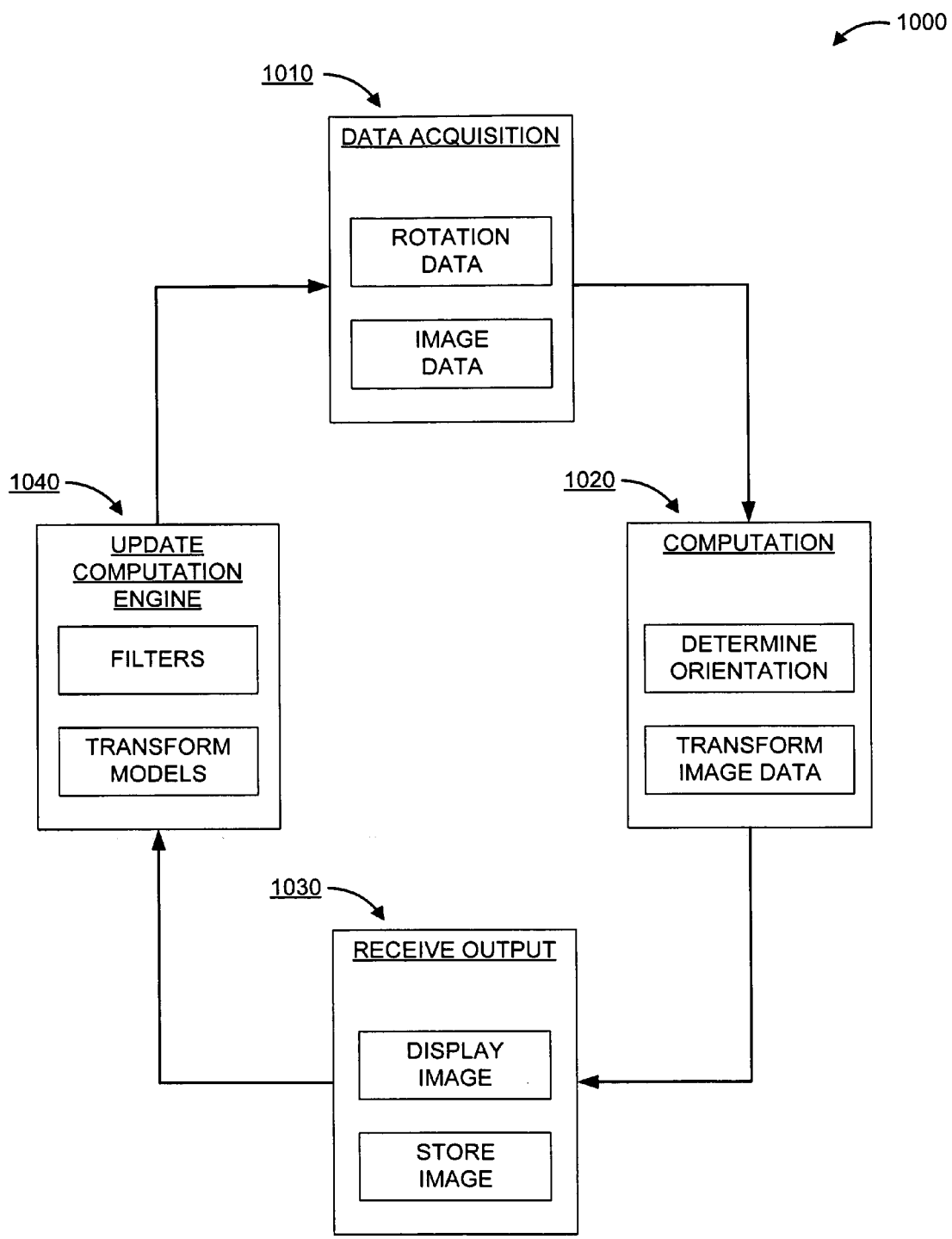
FIG. 10 is a process flow diagram illustrating various aspects of a system that is arranged to compensate and stabilize an image according to an embodiment.

FIG. 10 is a process flow diagram (1000) illustrating various aspects of a system that is arranged to compensate and stabilize an image, according to an embodiment. The illustrated process flow is broken into four functional groups. Initially, data acquisition is performed at step 1010. After data acquisition is complete, computation is performed at step 1020. Proceeding to step 1030, the processed image is received at an output. At step 1040, the computation engine is updated. Processing continues from step 1040 to step 1010, where the process flow repeats in a loop.

The data acquisition step (1010) includes the receipt of image data and rotation sensor data. The rotation sensor data can include positional information, angular information, acceleration information, or other appropriate data that is indicative of relative movement of the scope tip (e.g., accelerometer measurements, gyroscope measurements, etc.) such as previously described.

The computations step (1020) may include a determination of the orientation of the scope from the acquired rotation sensor data, and a selection/calculation of an appropriate transformation matrix based on the determined orientation of the scope. The computation step (1020) may also apply the selected transformation matrix to the acquired image data to provide transformed or processed image data.

The receive output step (1030) includes a number of facilities to utilize the processed image data such as displaying an image on a monitor, storing the processed image data in an image storage system, recording the image with a video recording device, etc.

The update computation engine step (1040) may include the collection of rotation sensor data and optionally applying procedures to the collected sensory data such as calculating data filters, adjusting transform models, as well as other procedures. The rotation sensor data may be acquired once per frame so that image correction can be properly performed without strange effects on the display. In other embodiments, the rotation sensor data can be acquired at a rate that is significantly higher (2×, 4×, etc.) than once per frame. Faster data acquisition can be useful for maintaining system models, calibration of instruments, dead reckoning on the instrument, as well as other purposes.

When it is desired to maintain an orientation (e.g., "upright") of the image with respect to the scope tip and local gravity, the data required from the rotation sensor can be angle with respect to gravity for any arbitrary datum associated with the instrument. When the instrument is parallel to gravity, a singularity may occur in the rotation sensor and there will be no de-rotation solution. To avoid a singularity, the control logic block is arranged to only apply orientation correction if the angle is not within some arbitrary amount of parallel to gravity.

Although the above described process steps imply an order of steps from step 1010 through step 1040 in sequence, the system is not so limited. Instead, the above-described steps may occur in any order and in some instance concurrently (e.g., parallel) or in pipelined configurations. Additional processes can also be included, where the total number of processes may be limited by the available bandwidth and computational capabilities of the specific implementation.

Example Frame Capture Systems

Figure 11:
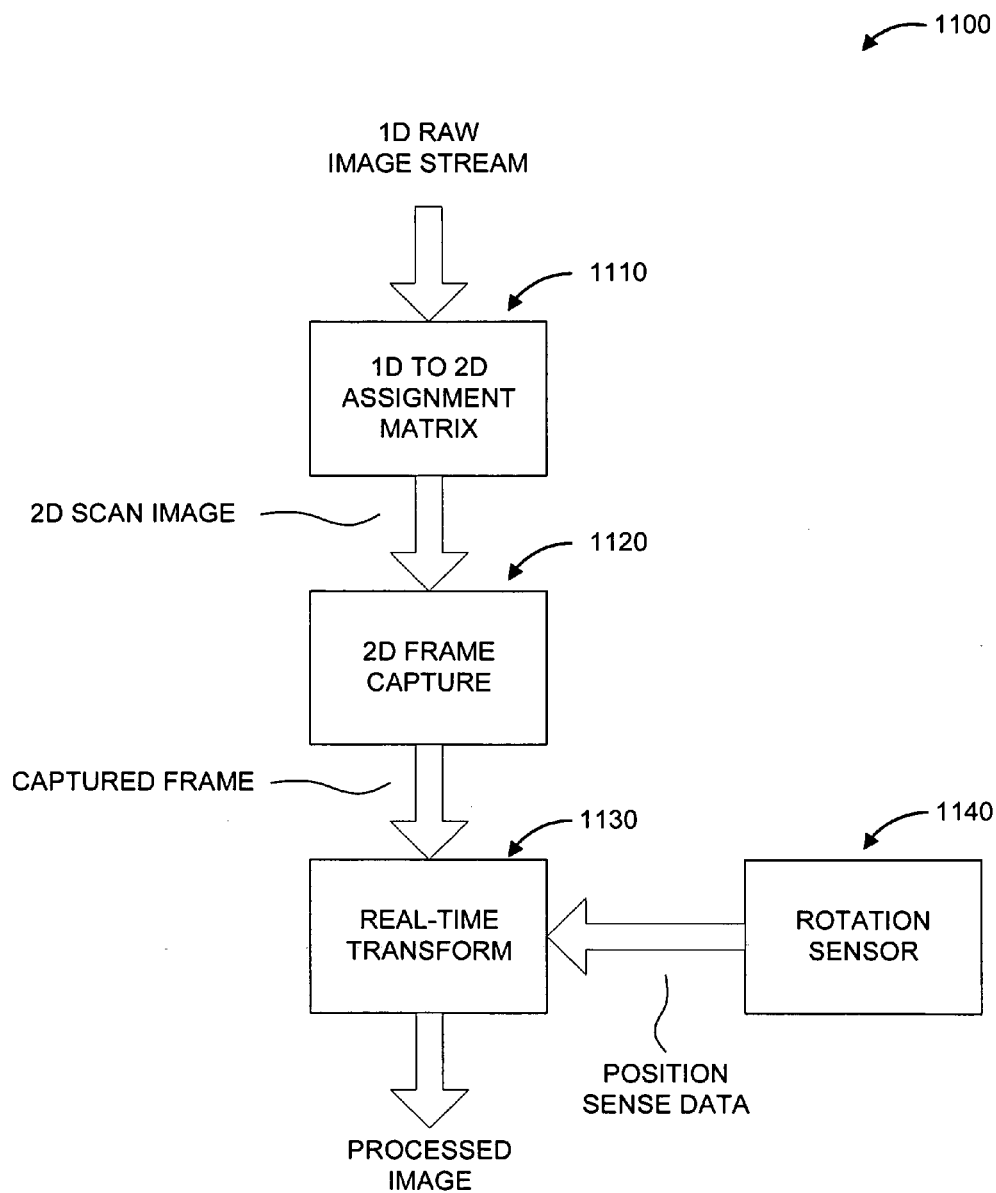
FIG. 11 is another illustrative block diagram for a system that is arranged to compensate and stabilize an image, wherein the rotation sensor is arranged to communicate positional information to the real-time transformation engine according to an embodiment.

FIG. 11 is another illustrative block diagram for a system (1100) that is arranged to compensate and stabilize an image, wherein the rotation sensor is arranged to communicate positional information to the real-time transformation engine, according to an embodiment. System 1100 includes a 1D to 2D assignment matrix block (1110), a 2D frame capture block (1120), a real-time transform block (1130), and a rotation sensor block (1140).

In some embodiments, the 1D to 2D assignment matrix block (1110) is arranged to receive a 1D image stream and provide a 2D scan image by assigning received data items (e.g., pixel data) to a corresponding 2D location in a matrix. The 2D frame capture block (1120) may be arranged to receive the 2D scan image and provide buffering and capturing functions, resulting in the captured frame. The real-time transform block (1130) can be arranged to receive position sense data from the rotation sensor block (1140), adjust the necessary rotational matrix coefficients based on the position sense data received, and apply a data transformation to the captured frame to provide a processed image. The processed image that is provided by the real-time transform block (1130) can be rotation and motion free as previously described.

Figure 12:
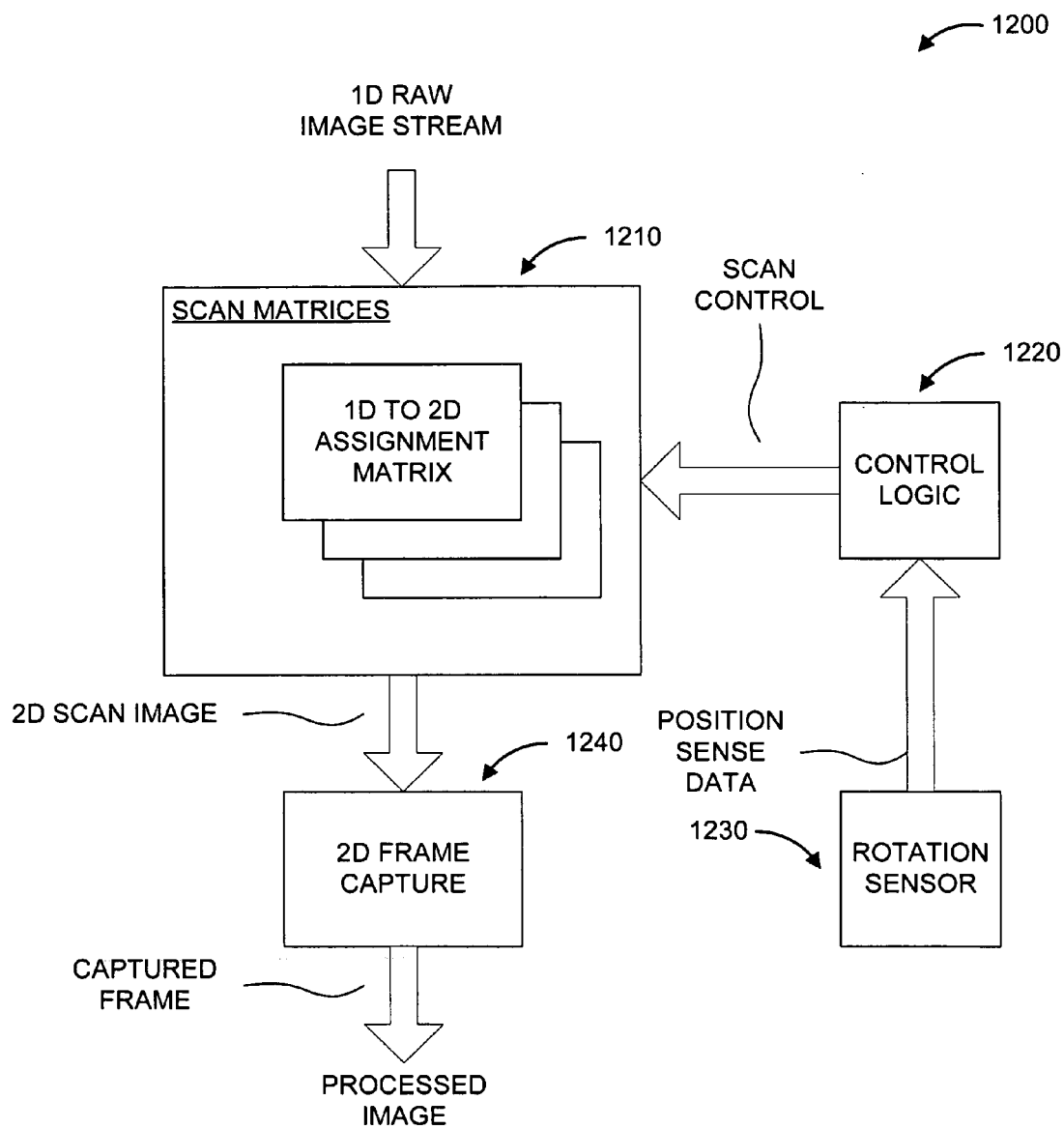
FIG. 12 is another illustrative block diagram for a system that is arranged to select one of a multiplicity of transformation matrices in response to positional information from the rotation sensor; arranged according to at least one embodiment of the present disclosure.

FIG. 12 is another illustrative block diagram for a system that is arranged to select one of a multiplicity of transformation matrices in response to positional information from the rotation sensor, according to at least one embodiment. System 1200 includes a set of scan matrices (1210), a control logic block (1220), a rotation sensor block (1230), and a 2D frame capture block (1240).

In one embodiment, the scan matrices (1210) may be arranged to provide for real time processing as the image is being scanned. The scan matrices (1210) may include a multiplicity of 1D to 2D assignment matrices that are arranged to receive a 1D image stream and may be configured to provide a 2D scan image when selected. The assignment matrices are configured to assign received data items (e.g., pixel data) to a corresponding 2D location in a matrix based on the desired scan pattern when selected. The selection of the assignment matrix from the scan matrices (1210) may be provided by a scan control signal from the control logic block (1220). The control logic block (1220) may be configured to adjust the selection of the scan control signal based on the received position sense data from the rotation sensor (1230). The 2D frame capture block (1240) can be arranged to receive the 2D scan image from the selected scan and provide buffering and capturing functions, resulting in the captured frame, which corresponds to the transformed or processed image data. For this example, the real-time transform is provided by the assignment matrix.

In a further example, not illustrated, the drive signals to a scanner device such as a MEMS scanner can be changed to effectively rotate the scan pattern for the image scanner device off-axis. The amount of off-axis rotation of the image scan plane for the image scanner device can be determined by the rotation matrices as previously described.

The above-described rotation sensor implementations are intended to serve as examples that can be used for determining position information of the scope and other examples are also contemplated. The rotation sensor itself may be located in the tip region of the scope, in the control body (e.g., in a handle of a hand-tool), along the shaft of the scope when the scope is a rigid device, or another appropriate location that will result in accurate position information.

Although the invention has been described herein by way of exemplary embodiments, variations in the structures and methods described herein may be made without departing from the spirit and scope of the invention. For example, the positioning of the various components may be varied. Individual components and arrangements of components may be substituted as known to the art. Since many embodiments of the invention can be made without departing from the spirit and scope of the invention, the invention is not limited except as by the appended claims.

What is claimed is:

1. An image processing system for stabilizing and compensating image rotations, the image processing system comprising:
    a console that is arranged to provide a processed image by applying a rotation matrix to image data in real-time, wherein the console is arranged to select the rotation matrix in response to positional information, wherein the console is further arranged to identify a singularity associated with the positional information such that the rotation matrix will not be altered when the singularity is identified;
    a scope that comprises a tubular body with a distal tip;
    a control body that is arranged in cooperation with the scope for guiding the scope during operation;
    a video capture device that is located within one of the control body, the tubular body and the distal tip of the scope, wherein the video capture device is arranged to provide the image data associated with a field of view; and
    a rotation sensor that is located within at least one of the control body and the scope, wherein the rotation sensor is arranged to determine the positional information and communicate the positional information to the console.

2. A method for stabilizing and compensating image rotations in an image processing system, the method comprising:
    acquiring positional information from a rotation sensor, wherein the positional information is associated with a rotational position of a scope in the image processing system, and wherein acquiring positional information from the rotation sensor comprises: acquiring positional information from a gyroscope that is located within a body of the scope such that the orientation of the body of the scope can be determined from the acquired positional information;
    acquiring image data from the scope;
    determining an orientation of the scope from the acquired positional information, wherein the orientation is determined relative to an artificial horizon;
    selecting a rotation matrix from the determined orientation, wherein selecting the rotation matrix from the determined orientation comprises: selecting one of a multiplicity of scan matrices based on the determined orientation; and
    applying the rotation matrix to the acquired image data to provide processed image data, wherein the processed image data does not rotate relative to the artificial horizon.

3. The method of claim 2, wherein acquiring image data comprises at least one of: assigning pixels from the image data to appropriate 2D locations in a scan image based on the selected one of the multiplicity of scan matrices, and capturing the 2D scan image data.

4. A method for stabilizing and compensating image rotations in an image processing system, the method comprising:
    acquiring positional information from a rotation sensor, wherein the positional information is associated with a rotational position of a scope in the image processing system, and wherein acquiring positional information from the rotation sensor comprises: acquiring positional information from a gyroscope that is located within a body of the scope such that the orientation of the body of the scope can be determined from the acquired positional information;
    acquiring image data from the scope;
    determining an orientation of the scope from the acquired positional information, wherein the orientation is determined relative to an artificial horizon;
    selecting a rotation matrix from the determined orientation; and
    applying the rotation matrix to the acquired image data to provide processed image data, wherein the processed image data does not rotate relative to the artificial horizon;
    identifying a singularity associated with the acquired positional information, and maintaining the rotation matrix when the singularity is identified.

5. The method of claim 4, wherein identifying the singularity comprises:
    evaluating an angle associated with the acquired positional information, and determining if the evaluated angle is within a range of values that is associated with an axis parallel to gravity.

6. An image processing system for stabilizing and compensating image rotations, the image processing system comprising:
    a console that includes a real-time transformation block that is arranged to apply assign each pixel from a 1D image data stream to a location in a 2D scan image according to a scan assignment matrix, and wherein the real-time transformation block is arranged such that the 2D scan image is de-rotated in response to sensed positional information, wherein the console is further arranged to select the scan assignment matrix by selecting one of a multiplicity of previously calculated scan matrices in response to the sensed positional information;
    a scope that comprises a body with a distal tip;
    a video capture device that is located within the body of the scope, wherein the video capture device is arranged to provide the 1D image data stream from an image that is observed in a field of view;
    a control body that is arranged in cooperation with the scope for guiding the scope during operation, wherein the control body is coupled to the console; and
    a rotation sensor that is located within at least one of the control body and the body of the scope, wherein the rotation sensor is arranged to sense the positional information and communicate the sensed positional information to the console.

* * * * *

UNITED STATES PATENT AND TRADEMARK OFFICE
Certificate

Patent No. 7,783,133 B2                                                             Patented: August 24, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Robert J. Dunki-Jacobs, Mason, OH (US); Frank B. Metting, III, Bothell, WA (US); Selso Luanava, Woodinville, WA (US); and Michael P. Weir, Blanchester, OH (US).

Signed and Sealed this Eighth Day of March 2011.

MATTHEW C. BELLA
*Supervisory Patent Examiner*
Art Unit 2624
Technology Center 2600